(12) United States Patent
Kriel et al.

(10) Patent No.: US 9,945,821 B2
(45) Date of Patent: Apr. 17, 2018

(54) COMPOSITE SAMPLING OF FLUIDS

(71) Applicant: SGS North America Inc., Rutherford, NJ (US)

(72) Inventors: Wayne A. Kriel, Friendswood, TX (US); Sven Lataire, Zevergem (BE)

(73) Assignee: SGS North America Inc., Rutherford, NJ (US)

( * ) Notice: Subject to any disclaimer, the term of this patent is extended or adjusted under 35 U.S.C. 154(b) by 114 days.

(21) Appl. No.: 14/804,846

(22) Filed: Jul. 21, 2015

(65) Prior Publication Data

US 2015/0323508 A1 Nov. 12, 2015

Related U.S. Application Data

(63) Continuation of application No. 13/750,710, filed on Jan. 25, 2013, now Pat. No. 9,097,695.
(Continued)

(51) Int. Cl.
*G01N 1/16* (2006.01)
*G01N 30/28* (2006.01)
(Continued)

(52) U.S. Cl.
CPC .............. *G01N 30/28* (2013.01); *G01N 1/22* (2013.01); *G01N 1/2247* (2013.01); *G01N 1/24* (2013.01);
(Continued)

(58) Field of Classification Search
CPC ..... G01N 1/10; G01N 2001/1093; G01N 1/16
See application file for complete search history.

(56) References Cited

U.S. PATENT DOCUMENTS 2,458,498 A   1/1949   Bergstrom
5,660,617 A   8/1997   Hatton
(Continued)

FOREIGN PATENT DOCUMENTS

CN   101300486 A   11/2008
RU   1994015270 A   4/1996
(Continued)

OTHER PUBLICATIONS

International Search Report and Written Opinion for International Application No. PCT/US2013/023220 dated May 2, 2013, 11 pages.
(Continued)

*Primary Examiner* — Hezron E Williams
*Assistant Examiner* — Alex Devito
(74) *Attorney, Agent, or Firm* — Fish & Richardson P.C.

(57) ABSTRACT

Composite sampling of a fluid flowing through a conduit includes collecting, in a vessel coupled to the conduit through which the fluid is flowing, a first discrete sample of fluid from the conduit, the first discrete sample having a first selected volume, and collecting, in the vessel and at a first interval from the first sample, a second discrete sample of the fluid from the conduit, the second discrete sample having a second selected volume, thereby forming a composite sample in the vessel while the vessel is coupled to conduit. The composite sample includes the first discrete sample and the second discrete sample, and may include one or more additional discrete samples. An apparatus for collecting the composite sample includes a gas chromatograph, and is arranged such that the composite sample is provided to the gas chromatograph without removing the composite sample from the apparatus or transporting the composite sample.

17 Claims, 9 Drawing Sheets

Related U.S. Application Data

(60) Provisional application No. 61/591,809, filed on Jan. 27, 2012.

(51) Int. Cl.
*G01N 1/24* (2006.01)
*G01N 1/22* (2006.01)
*G01N 30/06* (2006.01)
*G01N 33/22* (2006.01)
G01N 30/02 (2006.01)
G01N 1/10 (2006.01)

(52) U.S. Cl.
CPC .......... *G01N 30/06* (2013.01); *G01N 33/225* (2013.01); *G01N 2001/105* (2013.01); *G01N 2001/1093* (2013.01); *G01N 2030/025* (2013.01)

(56) References Cited

U.S. PATENT DOCUMENTS

| | | | |
|---|---|---|---|
| 5,753,832 A | 5/1998 | Bromberg et al. | |
| 6,094,968 A * | 8/2000 | Scheufler | G01N 1/26 702/77 |
| 7,874,221 B1 | 1/2011 | Mayeaux | |
| 8,991,233 B2 | 3/2015 | Kriel et al. | |
| 2004/0035183 A1 | 2/2004 | O'Brien et al. | |
| 2005/0217351 A1 | 10/2005 | Kreck et al. | |
| 2008/0092627 A1 | 4/2008 | Hadley et al. | |
| 2010/0012201 A1* | 1/2010 | Welker | G01N 1/10 137/535 |
| 2010/0213365 A1 | 8/2010 | Crowley et al. | |

FOREIGN PATENT DOCUMENTS

| | | |
|---|---|---|
| SU | 1354054 A1 | 11/1987 |
| SU | 1536249 A1 | 1/1990 |
| UA | 82818 C2 | 5/2008 |
| WO | WO2007/028130 A2 | 3/2007 |

OTHER PUBLICATIONS

Written Opinion of the International Preliminary Examining Authority issued in International Application No. PCT/US2013/023220 dated Feb. 13, 2014, 5 pages.

International Preliminary Report on Patentability issued in International Application No. PCT/US2013/023220 dated Jun. 2, 2014, 7 pages.

* cited by examiner

COMPOSITE SAMPLING OF FLUIDS

CROSS REFERENCE TO RELATED APPLICATION

This application is a continuation application of and claims priority to U.S. patent application Ser. No. 13/750,710 filed on Jan. 25, 2013, which claims priority to U.S. Application Ser. No. 61/591,809 entitled "Composite Sampling of Fluids" and filed on Jan. 27, 2012, both of which are incorporated herein by reference in their entirety.

TECHNICAL FIELD

This disclosure relates to formation and analysis of a composite sample of a fluid.

BACKGROUND

Analysis is performed on a variety of fluids transferred through conduits to assess various features of the fluid, including composition, impurity levels, and the like. One example includes compositional analysis of liquefied natural gas (LNG) to determine its commercial value. Many natural gas reserves are found in remote or offshore locations, and the natural gas is transported globally to market areas via LNG ships. Natural gas is transported under conditions that allow for a volumetric ratio of 600 times that of the product at standard temperature and pressure conditions. This is achieved with storage conditions of −162° C. Large ships of this type carry 2 to 3 billion cubic feet of natural gas. Compositional analyses performed on LNG yields calculated values including: gas compressibility, specific gravity, British thermal unit (BTU) value, gallons of liquid per thousand cubic feet (GPM), Wobbe index, methane number, and dew point. While vessels and terminal facilities have testing capabilities to perform such compositional analyses of LNG, the analyses are typically limited, and whole shipments may be erroneously assumed to be fairly uniform in composition for simplicity.

SUMMARY

In one aspect, an apparatus includes an inlet configured to receive a portion of a fluid flowing through a conduit, a valve coupled to the inlet, a pump coupled to the valve, a vessel coupled to the valve, and a gas chromatograph coupled to the valve. The apparatus is configured to collect a composite sample in the vessel, the composite sample including two or more discrete samples of the fluid, each of the discrete samples collected at a selected interval from at least one other discrete sample and having a selected volume.

Implementations may include one or more of the following features. For example, in some cases, the apparatus transfers the composite sample from the vessel to the gas chromatograph through the valve. The volume of each of the discrete samples is user-selectable. In certain cases, the volume of each of the discrete samples is selected to be the same. The selected interval may be based on elapsed time, and may correspond to a sampling rate of the pump. The sampling rate of the pump may be user-selectable. In some examples, the pump is a syringe pump. The syringe pump may be programmable.

The vessel is removably coupled to the valve. For example, the vessel may be coupled to the valve with a quick-connect fitting, such that the composite sample can be retained and/or transported off-site (e.g., for additional analysis) after collection and/or analysis by the gas chromatograph. The gas chromatograph is also coupled to the inlet, and the apparatus delivers a non-composite sample of the fluid flowing through the conduit to the gas chromatograph. Thus, a spot sample can be analyzed before, during, or after collection of a discrete sample for the composite sample. The apparatus may include an additional inlet for receiving an additional fluid from an additional source, wherein the gas chromatograph is coupled to the additional inlet and receives a sample of the additional fluid. The additional fluid may be, for example, one of several transfer lines from a ship carrying liquefied natural gas to a terminal facility. The apparatus can assess the composition of the composite sample, the non-composite sample, and/or the sample of the additional fluid.

The apparatus automatically collects the two or more discrete samples of the fluid in the vessel. The apparatus may further include a user interface and a controller, the controller operatively coupled to the valve, the pump, and the gas chromatograph and configured to control collecting the two or more discrete samples of the fluid in the vessel. In some cases, the apparatus is coupled to a computer, to allow for remote actuation or programming of the apparatus and/or additional data processing.

The apparatus is portable and may be self-contained. In one example, the apparatus is continuously operable in the absence of an external power source for at least 6-8 hours. In some cases, outside line power is supplied to the apparatus via a power cord. The portable apparatus allows rapid sampling and analysis of a variety of fluids (liquids, cryogenic liquids, gases) at remote locations.

In another aspect, collecting a composite sample of a fluid includes collecting, in a vessel coupled to a conduit through which a fluid is flowing, a first discrete sample of fluid from the conduit, the first discrete sample having a first selected volume, and collecting, in the vessel and at a first interval from the first sample, a second discrete sample of the fluid from the conduit, the second discrete sample having a second selected volume, thereby forming a composite sample in the vessel while the vessel is coupled to conduit, the composite sample including the first discrete sample and the second discrete sample. Thus, a composite sample is automatically collected in one vessel coupled to a conduit (e.g., the vessel may be part of an apparatus coupled to a conduit), without separately collecting and transferring multiple samples from a first container to a second container.

Implementations include one or more of the following features. The first interval may be based on elapsed time. For example, fluid flowing through the conduit may be sampled at a pre-selected sampling rate. In some cases, the composite sample is collected and transported to a second location for analysis. In certain cases, a composition of the composite sample is assessed without transporting the sample and/or without uncoupling the vessel from the apparatus that provided the discrete samples to the vessel. For example, a composition of the composite sample can be assessed while the vessel is coupled to the conduit, while the vessel is coupled to an apparatus coupled to the conduit, or while the vessel is coupled to a portion of an apparatus (e.g., a valve) that was coupled to the conduit during collection of the composite sample. Assessing a composition of the composite sample may include providing the composite sample to a gas chromatograph coupled to the conduit, or coupled to the vessel during collection of the composite sample. When the fluid is a liquid (e.g., a cryogenic liquid such as liquefied natural gas), the fluid is vaporized before introducing the sample to the gas chromatograph or before the discrete samples are collected in the vessel.

In some cases, one or more additional discrete samples of the fluid from the conduit are collected in the vessel at one or more additional intervals from the first discrete sample, thereby adding the one or more additional discrete samples of the fluid to the composite sample in the vessel before assessing the composition of the composite sample. In certain cases, a sample of the fluid flowing through the conduit is provided to a gas chromatograph coupled to the conduit (or the vessel). This feature allows assessment of spot samples of the fluid during collection of the composite sample. If the fluid is a liquid, the fluid is vaporized before the composition of the spot sample is assessed.

In another aspect, an apparatus includes an inlet configured to receive a portion of a fluid flowing through a conduit, a valve coupled to the inlet, a pump coupled to the valve, a vessel coupled to the valve, a gas chromatograph coupled to the valve, and a controller operatively coupled to the valve, the pump and the gas chromatograph. The controller is configured to provide, to the vessel, two or more discrete samples of the fluid flowing through the conduit, each of the discrete samples collected at a selected time interval from at least one other discrete sample, thereby forming a composite sample in the vessel.

Implementations may include one or more of the following features. For example, the controller may be further configured to transfer the composite sample from the vessel to the gas chromatograph while the vessel is coupled to the valve. The controller is operable to control the volume of each of the discrete samples, the selected time interval, or both.

The apparatus may further include a pressure regulator, a vaporizer, or both between the inlet and the valve. In some cases, the gas chromatograph is coupled to the inlet and the processor is further configured to provide a non-composite sample of the fluid flowing through the conduit to the gas chromatograph. The apparatus may also include an additional inlet for receiving an additional fluid from an additional conduit. The gas chromatograph is coupled to the additional inlet and receives a sample of the additional fluid from the additional conduit.

The apparatus is operable to assess the composition of the composite sample, the non-composite sample, and the sample of the additional fluid. The apparatus is self-contained and portable, and may further include a computer operatively coupled to the controller.

As described herein, composite sampling allows automatic, real-time collection of a composite sample of a fluid flowing through a conduit, so that composite properties of the fluid may be assessed. Collection of the composite sample as described allows for efficient, accurate assessment of composite properties of a large stream of fluid, and retention of a composite sample as needed for later analysis. Real-time analysis of spot samples provides additional information as the fluid flows through the conduit.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

BRIEF DESCRIPTION OF THE DRAWINGS

The concepts herein may be more completely understood in consideration of the following detailed description of various embodiments in connection with the accompanying drawings, in which.

DETAILED DESCRIPTION

Figure 1:
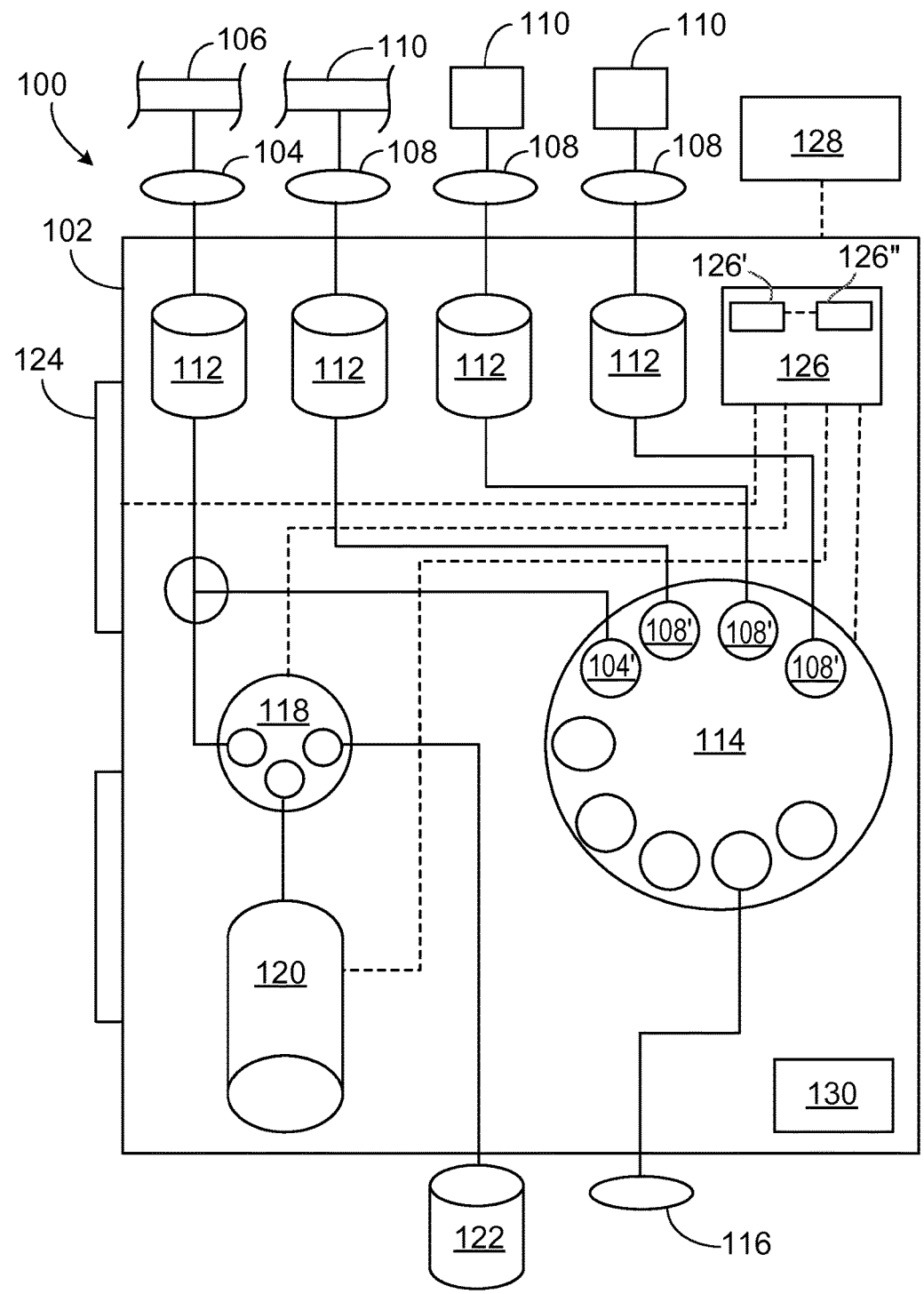
FIG. 1 depicts an apparatus for collecting and analyzing a sample of a fluid flowing through a conduit.

Analyzer 100, shown schematically in FIG. 1, can be used to collect and analyze spot and composite samples of a fluid flowing through a conduit according to standards known in the art, such as ASTM D1945, GPA 2261, D2163, and ISO 8943. Analyzer 100 can be used to assess properties such as composition (e.g., C1 to C5 hydrocarbons, C6+ hydrocarbons), BTU value, specific gravity, and Wobbe index, as well as the presence of impurities, such as $CO_2$ and $N_2$. The fluid may be, for example, liquefied natural gas (LNG), natural gas, liquefied petroleum gas (LPG), chemical gases (e.g., hydrocarbon gases, specialty gases, and landfill gas), shale gas, gas turbine fuel gas, well test gas, compressed gas liquids (CGL), or the like.

Analyzer 100 can be used for on-site, real-time determination of commercial value of a fluid (e.g., assessment or verification of ship/shore quality or aging of LNG), assessment of pipeline quality and gas blending (e.g., of natural gas), and detection of impurities or hazardous materials in the fluid. The analyzer can be used in a fixed location, to which samples are delivered for analysis, or as a self-contained unit in remote locations for on-site analysis, thereby obviating the need to transport samples for analysis. For on-site analysis, analyzer 100 can be hand carried to the site and coupled to a conduit (e.g., transfer line, pipeline, transport facility) by an operator. Analyzer 100 is powered by a battery pack and can operate continuously in the field for 6-8 hours or receives external line power via a power cord, automatically collecting a composite sample over the desired length of time and also analyzing samples directly from one or more conduits or fluid sources at pre-selected time intervals.

As shown in FIG. 1, analyzer 100 may be a portable, self-contained unit contained in a weather-resistant enclosure 102. Inlet 104 may be coupled to conduit 106, through which a fluid to be analyzed flows. In some cases, analyzer 100 includes one or more additional inlets 108, which may be coupled to one or more additional, discrete fluid sources 110. Each fluid source 110 may independently be, for example, a product conduit or a pressurized sample cylinder. Conduit 106 (and fluid source 110, if applicable) may be a fluid transfer line or a pipeline. Fluid flowing through conduit 106 (and fluid source 110, if applicable) may be from a common source (e.g., a vessel such as a tanker) or from separate, discrete sources. In some examples, the fluid flowing through conduit 106 (and 110, if applicable) is a liquid or cryogenic liquid (e.g., LNG). In other examples, the fluid flowing through conduit 106 (and 110, if applicable) is a gas (e.g., shale gas).

Fluid from inlet 104 flows to pressure regulator 112. In some cases, fluid from conduit 106 is provided to pressure regulator 112 at a pressure up to 3000 psig, and the fluid exits pressure regulator 112 at a pressure of 15 psig or less. In certain cases, for example, when the fluid in conduit 106 is a cryogenic liquid, regulator 112 may be heated, thereby functioning as a vaporizer. From pressure regulator 112, fluid from conduit 106 flows to gas chromatograph 114. Suitable gas chromatographs generally include a thermal conductivity detector (TCD) and a column set that provides separation of the parameters being assessed for a given fluid type.

Gas chromatograph 114 is configured in a static sampling configuration or a continuous flow configuration. In the static sampling configuration, sample gas does not flow continuously through gas chromatograph 114 prior to initiation of analysis. Rather, an amount of sample gas (e.g., approximately 50-100 cc) flows through gas chromatograph 114 prior to analysis. In the continuous flow configuration, sample gas flows through (e.g., bypasses) gas chromatograph 114 at a constant rate, and is directed to the column at selected sampling intervals. Thus, the continuous flow configuration allows for a thorough purge of the gas lines prior to the analysis of a sample. When the fluid is a cryogenic product, such as LNG, it may be preferable to operate gas chromatograph 114 in a continuous flow configuration so that suitable flow of the cryogenic product through regulator 112 (and thus proper gasification) is maintained. Waste from gas chromatograph 114 exits analyzer 100 through outlet 116.

For collection and analysis of a composite sample formed by combining two or more spot (or non-composite samples), fluid from regulator 112 flows to valve 118. In one example, valve 118 is a four-way valve. Pump 120 and vessel 122 are coupled to valve 118. In some cases, vessel 122 is removably coupled to valve 118 (e.g., with a quick-connect fitting). Pump 120 is a volumetric pump such as, for example, an automated sampling syringe with programmable withdrawal/infusion volumes and collection rate. Pump 120 is able to compress sampled fluid (i.e., gas), and can be used to evacuate portions of analyzer 100 (e.g., transfer lines). Suitable examples of pump 120 include a variety of programmable syringe pumps available from Harvard Apparatus (Holliston, Mass.). In one example, vessel 122 is a MiniCans™ MC450SQT available from Entech Instruments (Simi Valle, Calif.). In some cases, vessel 122 is located inside enclosure 102. In other cases, however, as shown in FIG. 1, vessel 122 is located outside enclosure 102, thereby facilitating decoupling of vessel 122 from analyzer 100 (e.g., from valve 118).

During operation of analyzer 100, pump 120 provides discrete samples of fluid from conduit 106 to vessel 122, thereby forming a composite sample in vessel 122. As used herein, a "composite sample" collected in vessel 122 generally includes two or more discrete samples of fluid from conduit 106, each discrete sample having a known volume, and each discrete sample taken from conduit 106 at a selected non-zero interval from at least one other discrete sample. The volumes of the discrete samples may be the same or different, and the interval between a first pair of discrete samples may be selected to be the same as or different than the interval between a second pair of discrete samples. The interval between two discrete samples can be based on an elapsed time between samples (e.g., a sampling rate), or on the volume of fluid flow through conduit 106. The volume of a discrete sample is typically in a range of 5 cc to 100 cc, or otherwise as suitable to a selected application. The sampling rate or interval between discrete samples can also be selected. In one example, a sample volume of 50 cc is collected at 1 hour intervals.

To collect a composite sample, valve 118 and pump 120 are operated such that a selected volume of the fluid is drawn into pump 120, and then transferred to vessel 122. This process is repeated at a selected interval, such that additional samples of the fluid are transferred to vessel 122, thereby forming a composite sample. Between (or during) the collection of two discrete samples in vessel 122, a non-composite or spot sample from conduit 106 may be analyzed by gas chromatograph 114.

A composite sample may include a multiplicity of spot (non-composite) samples collected over a length of time at a selected sampling rate. Thus, for a fluid such as LNG being transferred from a tanker to a terminal facility, a composite sample may be collected over the duration of the transfer process. In some cases, the sampling rate is selected to form a composite sample at selected discharge percentages from the vessel (e.g., 25% discharge, 50% discharge, and 75% discharge). After collection of the composite sample is complete, the composite sample is provided to gas chromatograph 114 through valve 118 and sample port 104', allowing analysis of the composite sample without decoupling vessel 122 from analyzer 100. That is, the composite sample is collected in real-time (spot or non-composite samples are combined to form the composite sample incrementally, as the fluid flows through conduit 106) and analyzed by analyzer 100 while vessel 122 is coupled to valve 118, without separating vessel 122 from analyzer 100. In some cases, a composite sample is transferred from vessel 122 through valve 118 to gas chromatograph 114 while analyzer 100 is coupled to conduit 106.

In some cases, it may be desirable to remove vessel 122 from analyzer 100 for sample retention and/or for additional analysis off-site. Additional analysis may include, for example, detection of sulfur compounds, ionic species, and/or select hydrocarbon species that are not identified by the column set on gas chromatograph 114.

One or more inlets 108 may be coupled to one or more fluid sources 110, respectively, for spot analysis of samples from the fluid sources in a manner similar to that described for spot analysis of fluid from conduit 106. Fluid sources 110 include, for example, a conduit through which a fluid flows, a cylinder containing a fluid, and the like. In certain cases, one or more inlets 108 may include a quick connect fitting to allow convenient coupling to a conduit or cylinder for spot analysis of fluid in the conduit or cylinder. Fluid from fluid sources 110 flows through pressure regulators 112, which may also serve as vaporizers, to sample ports 108' of gas chromatograph 114, for analysis. As with samples from conduit 106, gas chromatograph 114 may be programmed to analyze samples from fluid sources 110 at pre-selected intervals.

Analyzer 100 includes user interface 124 operatively coupled to one or more controller(s) 126. Controller(s) 126 have one or more processors 126' and memory units 126". Memory unit(s) 126" stores instructions to control chromatograph 114, valve 118, and pump 120, and controller(s) 126 cooperates with chromatograph 114, valve 118, and pump 120, such that the analyzer operates automatically to collect and analyze samples. Parameters (e.g., the sample stream to be analyzed and the mode of analysis (e.g., static or continuous flow operation) of gas chromatograph 114, the sampling rate and sample volume for the discrete samples to be collected in vessel 122 and the number of samples to be collected before the composite sample is provided to the gas chromatograph) may be pre-selected or input by a user. In some cases, processor(s) 126 is operatively coupled to computer 128, such that analyzer 100 is controlled remotely.

Analyzer 100 may include one or more batteries 130 for self-contained remote operation for a length of time (e.g., from 6-8 hours). Analyzer 100 may also include one or more battery back-ups for extended operation. In some cases, analyzer 100 is powered by line voltage via a power cord.

Figure 2:
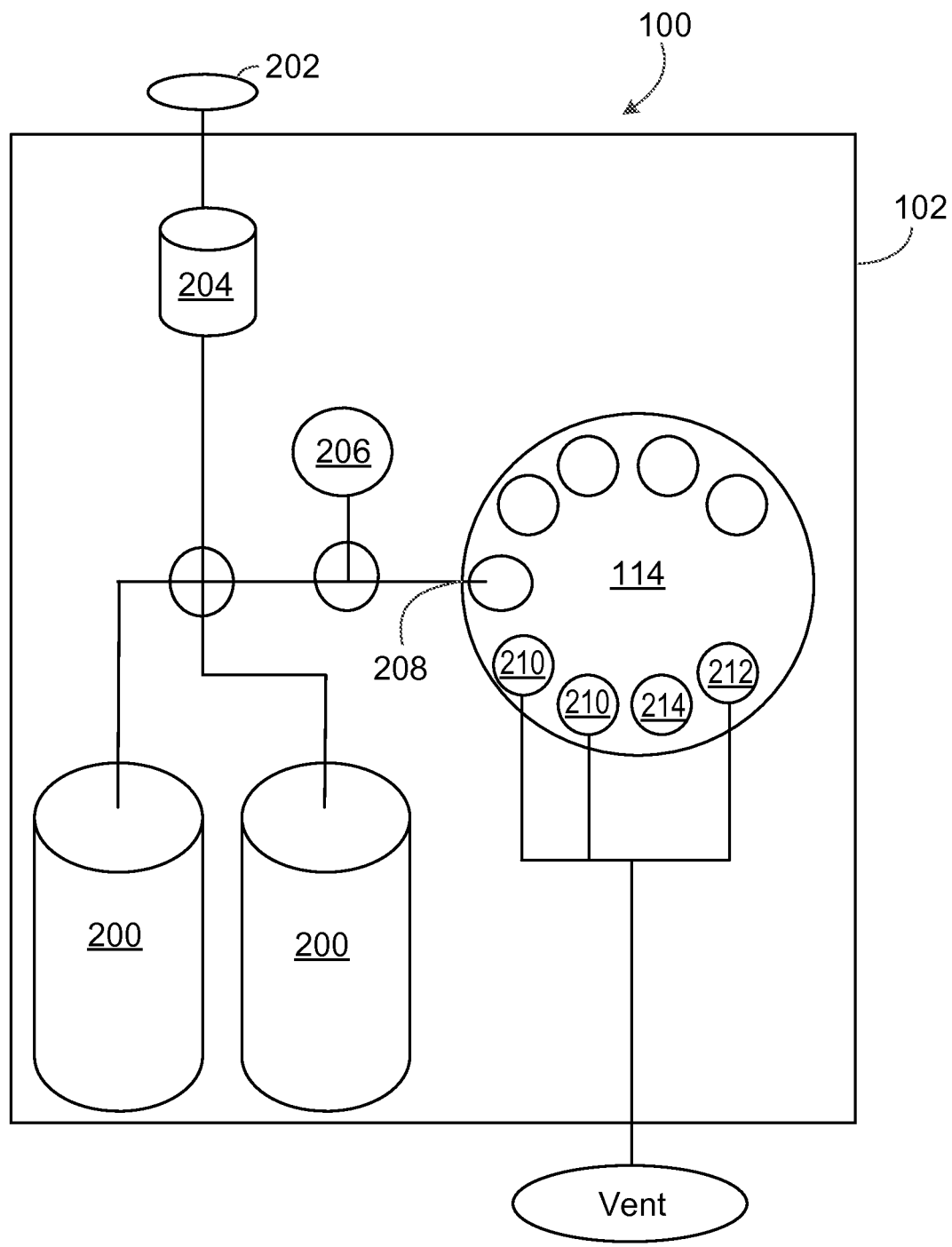
FIG. 2 depicts a carrier gas flow path for the apparatus shown in FIG. 1.

Helium may be used as a carrier gas for gas chromatograph 114. Helium allows for the operation of a thermal conductivity detector (TCD) in gas chromatograph 114, as well as a means to achieve component separation. FIG. 2 is a schematic diagram depicting carrier gas components of analyzer 100. As depicted in FIG. 2, analyzer 100 includes two helium reservoirs 200. Helium reservoirs 200 may have, for example, a total capacity of 224 liters of helium at standard temperature and pressure. This volume of helium can yield up to 6 days of continuous run time for analyzer 100. Helium reservoirs 200 may be filled through inlet 202. Backflow valve 204 is positioned inline, thereby inhibiting flow of helium from reservoirs 200 to inlet 202, and allowing reservoirs 200 to be directly filled with helium. Once the pressure stabilizes (e.g., at a maximum fill pressure of 1200 psig), the helium source may be disconnected from inlet 202.

Helium reservoirs 200 are installed in analyzer 100 with quick-connect fittings. The reservoirs are interchangeable and can be disconnected independently of one another, thereby providing additional helium without interrupting operation of analyzer 100. Depleted reservoirs 200 may be replaced with new or refilled reservoirs.

During operation, helium from helium reservoirs 200 flows past gauge 206 and into gas chromatograph 114 through sample inlet 208. Helium exits gas chromatograph 114 through column vents 210 and gauge port vent 212, and sample gas exits the gas chromatograph through sample vent 214.

Figure 3:
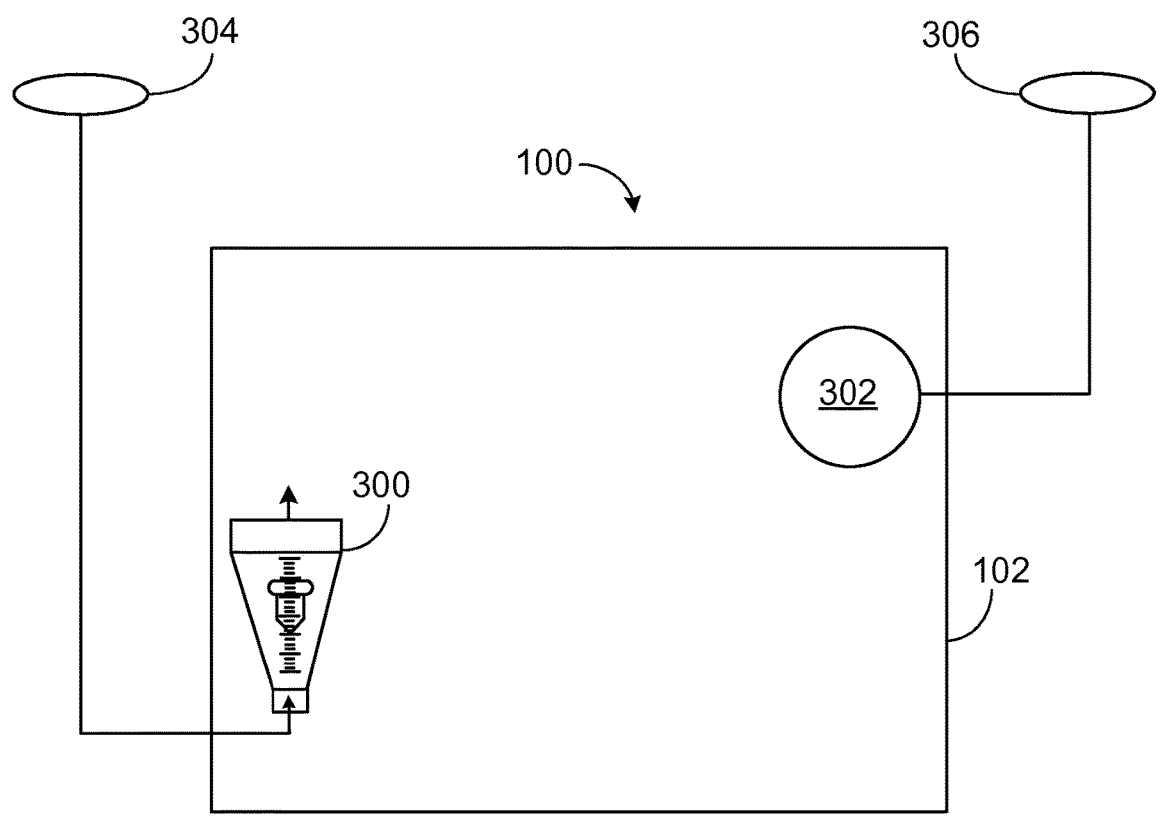
FIG. 3 depicts components designed to achieve a positive pressure enclosure for the apparatus shown in FIG. 1.

Analyzer 100 is designed with a positive pressure enclosure for operation in environments classified as) Class 1, Division 2 environments. FIG. 3 depicts components of a purge system in analyzer 100, including rotameter 300 and pressure gauge 302. Flow of inert gas (e.g., nitrogen or air) from a source coupled to inlet 304 into analyzer 100 is controlled by rotameter 300, and pressure gauge 302 monitors gas pressure in enclosure 102. A control valve on rotameter 300 is operated to achieve a flow of the inert gas through enclosure 102 sufficient to meet positive pressure requirements. Gas is vented through inert gas purge 306, which is coupled to pressure gauge 302.

Figure 4:
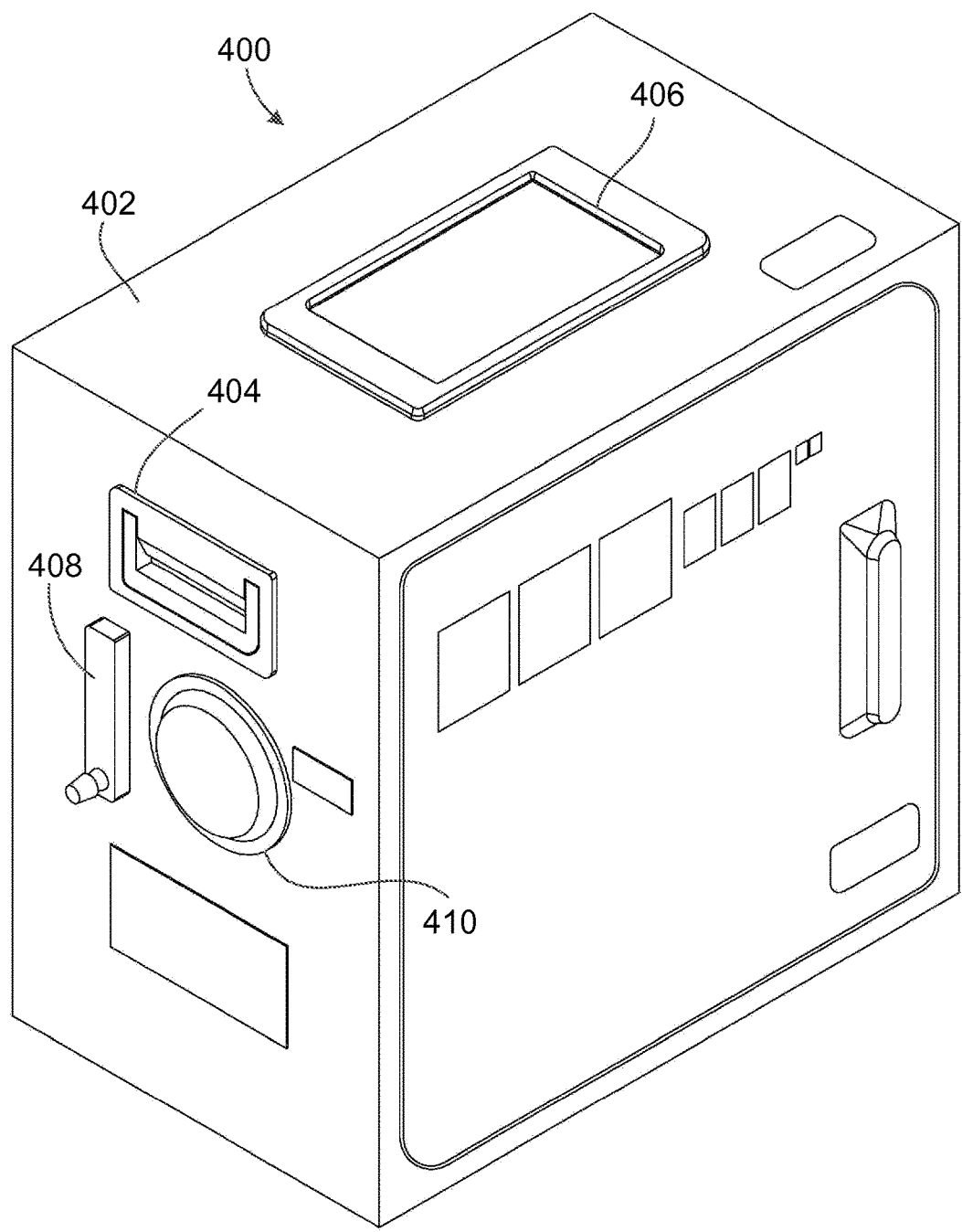
FIGS. 4 and 5 depict exterior views of an example of the apparatus shown in FIG. 1.
Figure 5:
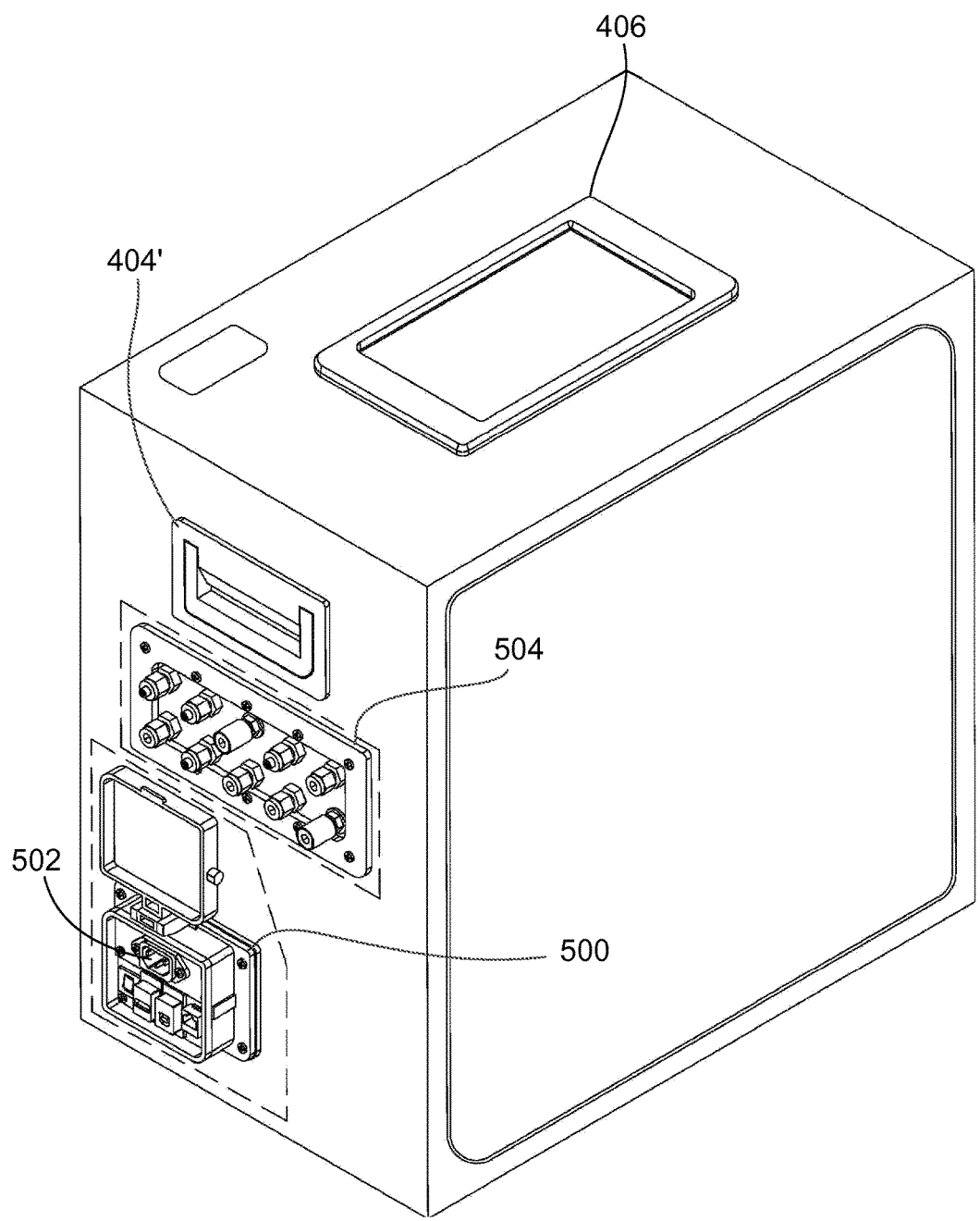

FIGS. 4 and 5 depict exterior views of analyzer 400, an example of analyzer 100 described with respect to FIGS. 1-3. As shown in FIG. 4, analyzer 400 includes enclosure 402 having dimensions of about 50 cm×50 cm×32 cm. Handle 404 facilitates portability of analyzer 400. Touch PC 406 corresponds to user interface 124 depicted in FIG. 1. Touch PC 406 may also include one or more controllers, processors, and/or memory units depicted in FIG. 1. Rotameter 408 and pressure gauge 410 correspond to rotameter 300 and pressure gauge 302 shown in FIG. 3. FIG. 5 shows another exterior view of analyzer 400, including Touch PC 406 and second handle 404' opposite handle 404 shown in FIG. 4. Electrical port 500 includes a 120 V AC electrical connector 502 through which, for example, analyzer 400 can be powered or one or more of batteries 130 depicted in FIG. 1 can be charged. Bulkhead panel 502 includes inlets (e.g., inlets corresponding to inlets 104 and 108 shown in FIG. 1, inlet 202 shown in FIG. 2, inlet 304 shown in FIG. 3, and inlets GC1-S1, GC2-S2, GC3-S3, CARRIER, PRG-IN, and CALGAS shown in FIG. 8) and outlets (e.g., outlets corresponding to outlet 116 shown in FIG. 1, outlet 214 shown in FIG. 2, outlet 306 shown in FIG. 3, and COMP-S1 and VACUUM shown in FIG. 8).

Figure 6:
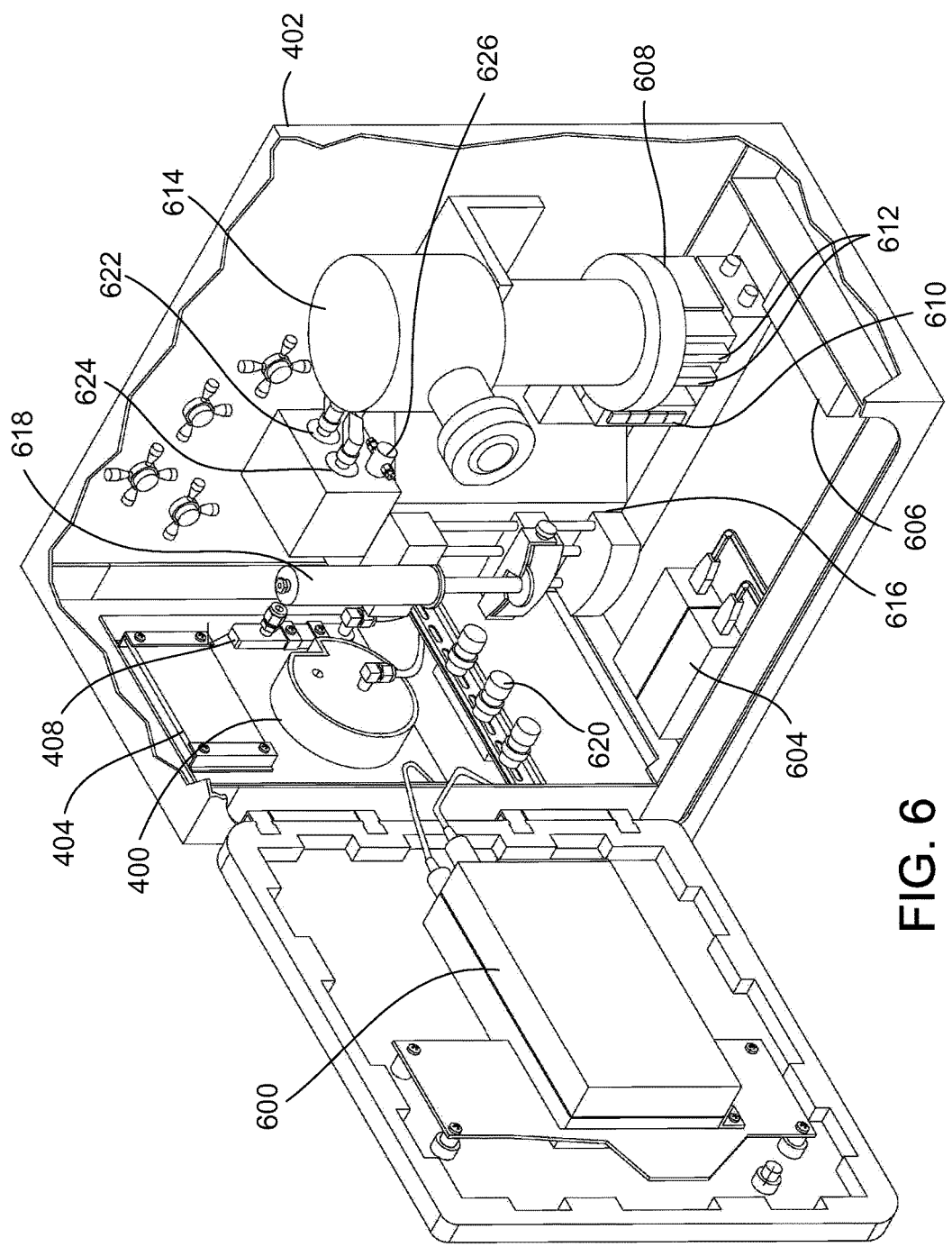
FIGS. 6 and 7 depict interior views of the apparatus shown in FIG. 4.
Figure 7:
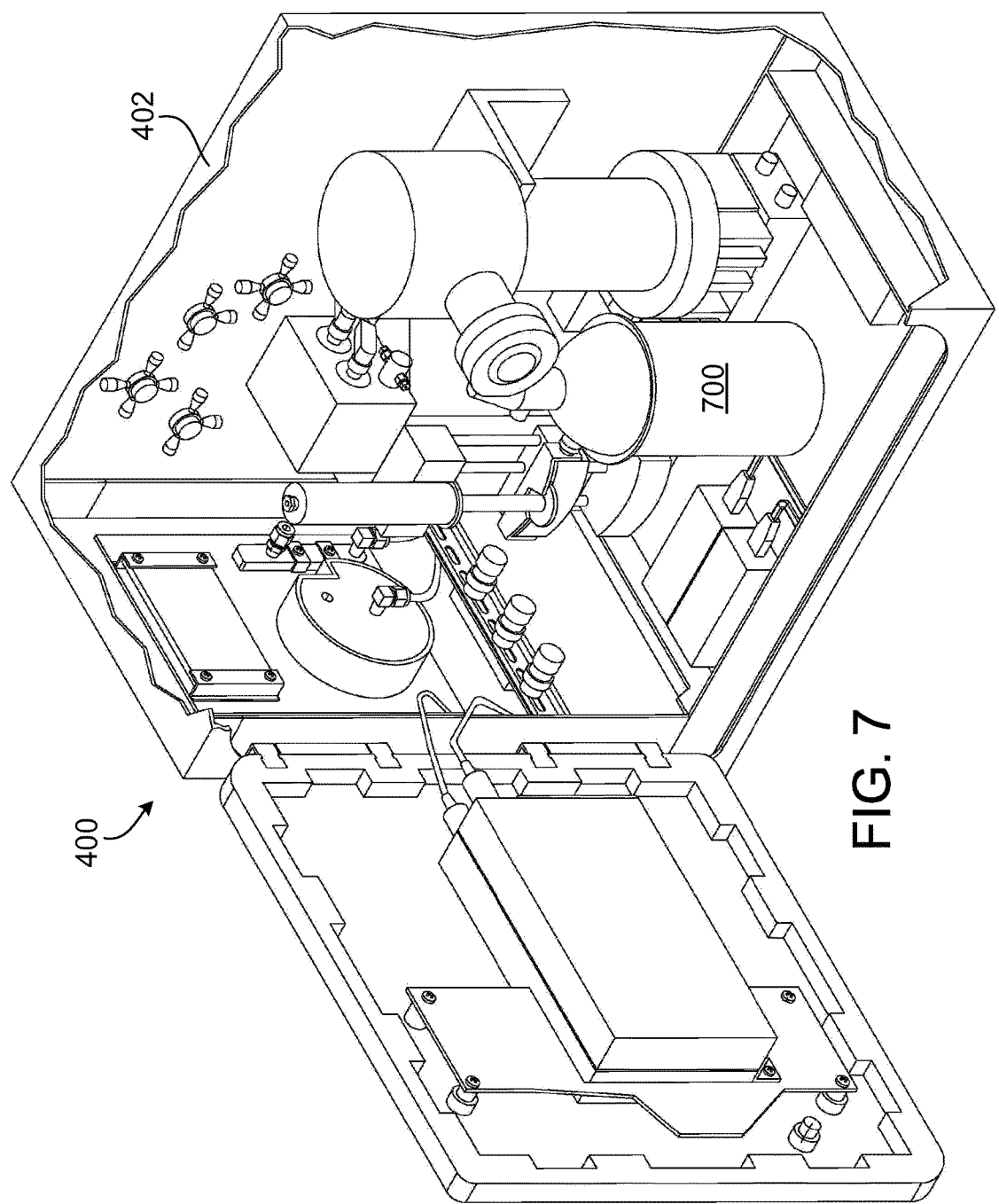

FIGS. 6 and 7 depict interior views of analyzer 400. Handle 404, rotameter 408, and pressure gauge 410 are visible inside enclosure 402. Battery 600 in door 602 of enclosure 402 corresponds to battery 130 in FIG. 1. Battery 600 may be, for example, a 14.8 VDC lithium ion battery. Analyzer 400 also includes power supply 604 and DC-DC converter 606 as well as digital acquisition unit 608, analog input module 610, and relay module 612. Power supply 604 may be, for example, a 120 VAC to 19 VDC power supply, and DC-DC converter 606 may be, for example, a 12V to 24V DC-DC converter. Gas chromatograph 614 corresponds to gas chromatograph 114 shown in FIG. 1. Programmable pump 616 and stainless steel syringe 618 together correspond to pump 120 shown in FIG. 1 and syringe/pump assembly 813 shown in FIG. 8. Two-way solenoid valve 620 corresponds to 2-way solenoid valves $804_1$, $804_2$, and $804_3$ shown in FIG. 8. Pressure transducers 622 (e.g., 0-100 PSIG) and 624 (e.g., 14.5-0 PSIG) are positioned proximate regulator 626, which corresponds to regulator 112 shown in FIG. 1. Regulator 626 may be, for example, a single stage regulator (e.g., 0-500 PSIG). FIG. 7 shows an interior view of analyzer 400 with helium reservoir 700 coupled to gas chromatograph 614. Helium reservoir 700 corresponds to one of helium reservoirs 200 shown in FIG. 2.

Figure 8:
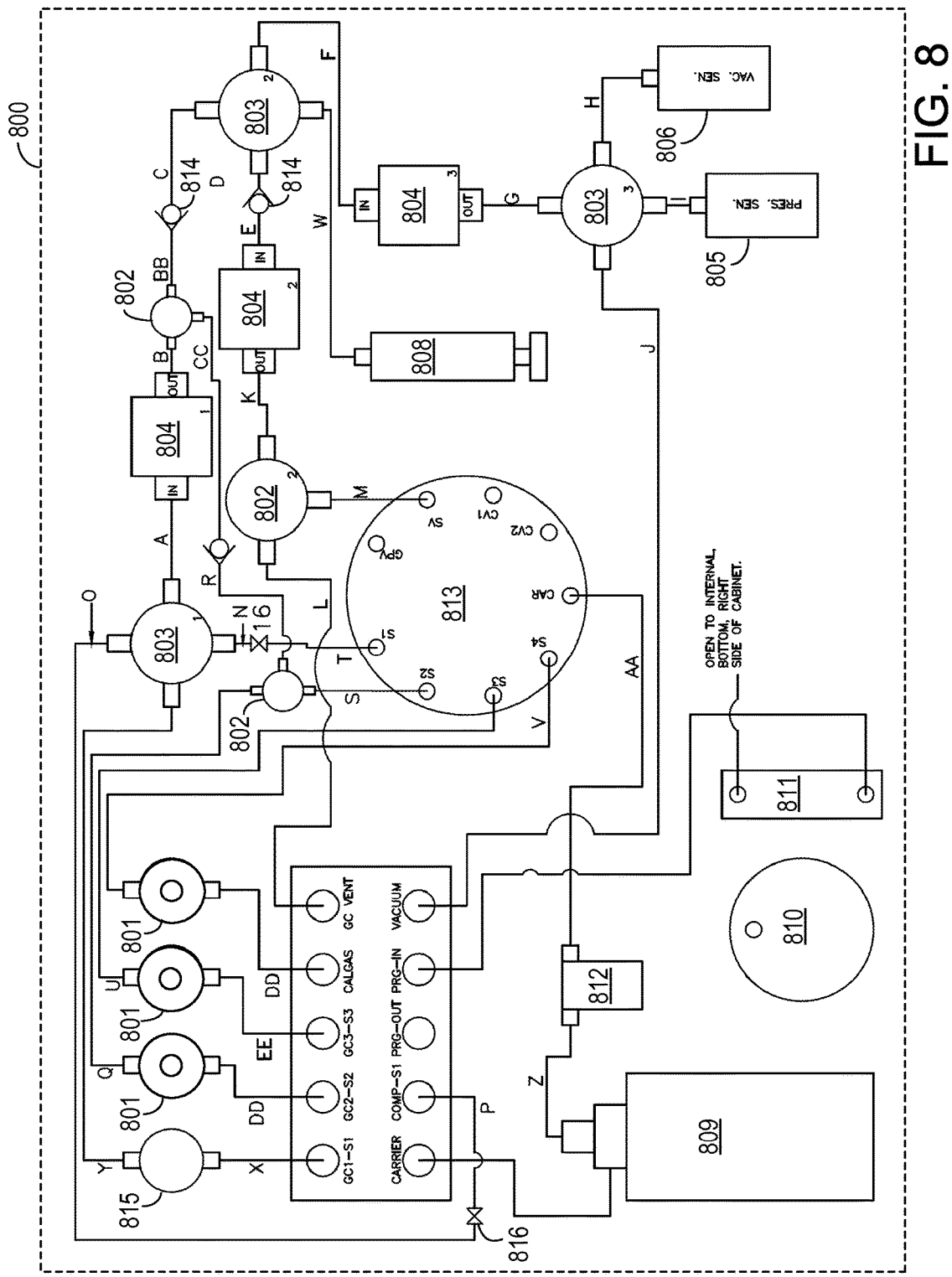
FIG. 8 depicts an example of a carrier gas flow path in an embodiment of an analyzer.

FIG. 8 is a schematic diagram showing an example of gas flow in analyzer 800, with needle valves 801, tee fittings 802, cross fittings 803, 2-way solenoid valves 804, pressure sensor 805, vacuum sensor 806, syringe/pump assembly 808, carrier gas reservoir 809, purge system 810, flow meter 811, pressure regulator 812, gas chromatograph 813, check valves 814, sampling accumulator (mixing can) 815, and metering valves 816. Inlet GC1-S1 may be coupled to a product conduit through which a fluid to be analyzed flows. In some cases, analyzer 800 includes one or more additional inlets (GC2-S2, GC3-S3, and CALGAS), which may be coupled to one or more additional, discrete fluid sources. Each fluid source may independently be a product conduit or a pressurized sample cylinder. The product conduit may be a fluid transfer line or a pipeline. Fluid flowing through the product conduit leading into the manifold may be from a common source (e.g., a tanker) or from separate, discrete sources. In some examples, the fluid flowing through a product conduit is a liquid or cryogenic liquid (e.g., LNG). In other examples, the fluid flowing through the product conduit is a gas (e.g., shale gas).

Fluid from inlet GC1-S1 flows to mixing can 815. In some cases, fluid from the product conduit will enter GC1-SI, GC2-S2, or GC3-S3 at a pressure up to 450 psig, and small-bore tubing and in-line hardware reduce the effective pressure to 15 psig or less. When the product conduit is sampled through GC1-S1 and enters mixing can 815, it then flows from mixing can 815 through cross fitting 803. From cross fitting $803_1$ the fluid passes through 2-way solenoid $804_1$, then through check valve 814. The fluid then passes through a second cross fitting $803_2$, through a second 2-way solenoid $804_2$, then through a tee fitting $802_2$. From that point the fluid enters gas chromatograph 813. Suitable gas chromatographs generally include a thermal conductivity detector (TCD) and a column set that provides separation of the parameters being assessed for a given fluid type.

Gas chromatograph 813 is configured in a static sampling configuration or a continuous flow configuration. In the static sampling configuration, sample gas does not flow continuously through gas chromatograph 813 prior to initiation of analysis. Rather, an amount of sample gas (e.g., approximately 50-100 cc) flows through gas chromatograph 813 prior to analysis. In the continuous flow configuration, sample gas flows through (e.g., bypasses) gas chromatograph 813 at a constant rate, and is directed to the column at selected sampling intervals. Thus, the continuous flow configuration allows for a thorough purge of the gas lines prior to the analysis of a sample. When the fluid is a cryogenic product, such as LNG, it may be preferable to operate gas chromatograph 813 in a continuous flow configuration so that suitable flow of the cryogenic product through the system tubing, fittings, and other system hardware is maintained for suitable vaporization. Waste from gas chromatograph 813 exits analyzer 800 through outlet COMP-S1.

For collection and analysis of a composite sample formed by combining two or more spot (or non-composite samples), fluid from flows through mixing can 815, through cross fitting $803_1$, through 2-way solenoid $804_2$, through check valve 814, through cross fitting $803_2$, and into syringe/pump assembly 808, which is an automated sampling syringe with programmable withdrawal infusion volumes and collection rates. A sample aliquot is then pushed by syringe/pump assembly 808 through cross fitting $803_2$, through 2-way solenoid $804_3$, through cross fitting $803_3$, then out to the manifold position labeled vacuum. The syringe/pump assembly 808 is able to compress sampled fluid (i.e., gas) and evacuate certain lines and containers (such as the composite sample collection container described in this paragraph. Suitable examples of a workable syringe/pump assembly include a variety of automatic syringe/pump systems available from Harvard Apparatus (Holliston, Mass.). A collection canister is attached to the manifold using a quick-connect type of connection. In one example, the canister is a MiniCans™ MC450SQT available from Entech Instruments (Simi Valle, Calif.). In some cases, the composite sample container may be located inside the analyzer enclosure. In other cases, however, the container for the composite sample is located outside the analyzer enclosure, thereby facilitating decoupling of the composite sample container from the analyzer.

During operation of analyzer, syringe/pump assembly 808 provides discrete samples of fluid from the product conduit to the composite sample canister, thereby forming a composite sample in the composite sample canister. As used herein, a "composite sample" collected in the composite sample canister generally includes two or more discrete samples of fluid from the product conduit, each discrete sample having a known volume, and each discrete sample taken from the product conduit at a selected non-zero interval from at least one other discrete sample. The volumes of the discrete samples may be the same or different, and the interval between a first pair of discrete samples may be selected to be the same as or different than the interval between a second pair of discrete samples. The interval between two discrete samples can be based on an elapsed time between samples (e.g., a sampling rate), or on the volume of fluid flow through the product conduit. The volume of a discrete sample is typically in a range of 5 cc to 100 cc, or otherwise as suitable to a selected application. The sampling rate or interval between discrete samples can also be selected. In one example, a sample volume of 50 cc is collected at 1 hour intervals.

To collect a composite sample, syringe/pump assembly 808 is operated such that a selected volume of the fluid is drawn into the syringe, and then transferred to the composite sample canister. This process is repeated at a selected interval, such that additional samples of the fluid are transferred to the composite sample canister, thereby forming a composite sample. Between (or during) the collection of two discrete samples in the composite sample canister, a non-composite or spot sample from the customer's product conduit may be analyzed by gas chromatograph 813.

A composite sample may include a multiplicity of spot (non-composite) samples collected over a length of time at a selected sampling rate. Thus, for a fluid such as LNG being transferred from a tanker to a terminal facility, a composite sample may be collected over the duration of the transfer process. In some cases, the sampling rate is selected to form a composite sample at selected discharge percentages from the vessel (e.g., 25% discharge, 50% discharge, and 75% discharge). After collection of the composite sample is complete, the composite sample is provided to gas chromatograph 813 through cross fitting $803_3$, 2-way solenoid $804_3$, cross fitting $803_2$, and into syringe/pump assembly 808. The sample is then discharged from syringe/pump assembly 808 into cross fitting $803_2$, through check valve 814, through 2-way solenoid $804_2$, through tee fitting $802_2$, and into gas chromatograph 813. The composite sample is collected in real-time (spot or non-composite samples are combined to form the composite sample incrementally, as the fluid flows through the product conduit) and analyzed by analyzer 800 while the composite sample canister is coupled to the valve and plumbing configuration described herein, without separating the composite sample canister from the analyzer. In some cases, a composite sample is transferred from the composite sample canister through GC2-S2 or GC3-S3 to gas chromatograph 813 while the analyzer is coupled to the product conduit through GC1-S1.

In some cases, it may be desirable to remove the composite sample canister from the analyzer for sample retention and/or for additional analysis off-site. Additional analysis may include, for example, detection of sulfur compounds, ionic species, and/or select hydrocarbon species that are not identified by the column set on gas chromatograph 813.

One or more inlets GC1-S1, GC2-S2, GC3-S3, and CAL-GAS may be coupled to one or more fluid sources, respectively for spot analysis of samples from the fluid sources in a manner similar to that described for spot analysis of fluid from the product conduit. Fluid sources include, for example, a conduit through which a fluid flows, a cylinder containing a fluid, and the like. In certain cases, one or more inlets may include a quick connect fitting to allow convenient coupling to a conduit or cylinder for spot analysis of fluid in the conduit or cylinder. As with samples from the product conduit described herein, gas chromatograph 813 may be programmed to analyze gaseous samples from other fluid sources at pre-selected intervals. The analyzer may be configured with additional mixing cans to handle multiple liquid samples.

Helium may be used as a carrier gas for gas chromatograph 813. Helium allows for the operation of a thermal conductivity detector (TCD) in gas chromatograph 813, as well as a means to achieve component separation. As depicted in FIG. 8, analyzer 800 includes one or more carrier gas (e.g., helium) reservoirs 809. Helium is typically used as the carrier gas. Carrier gas reservoir 809 may have, for example, a total capacity of 224 liters of helium at standard temperature and pressure. This volume of helium can yield up to 6 days of continuous run time for the analyzer. Carrier gas reservoir 809 may be filled through inlet CARRIER. Once the pressure stabilizes (e.g., at a maximum fill pressure of 1200 psig), the carrier gas source may be disconnected from inlet CARRIER. Carrier gas reservoir 809 is installed in analyzer 800 with quick-connect fittings. A depleted carrier gas reservoir 809 may be replaced with new or refilled reservoirs.

During operation, carrier gas from carrier gas reservoir 809 flows through pressure regulator 812 and into gas chromatograph 813 through inlet CAR. Carrier gas exits gas chromatograph 813 through vents described with respect to FIG. 2.

Figure 9:
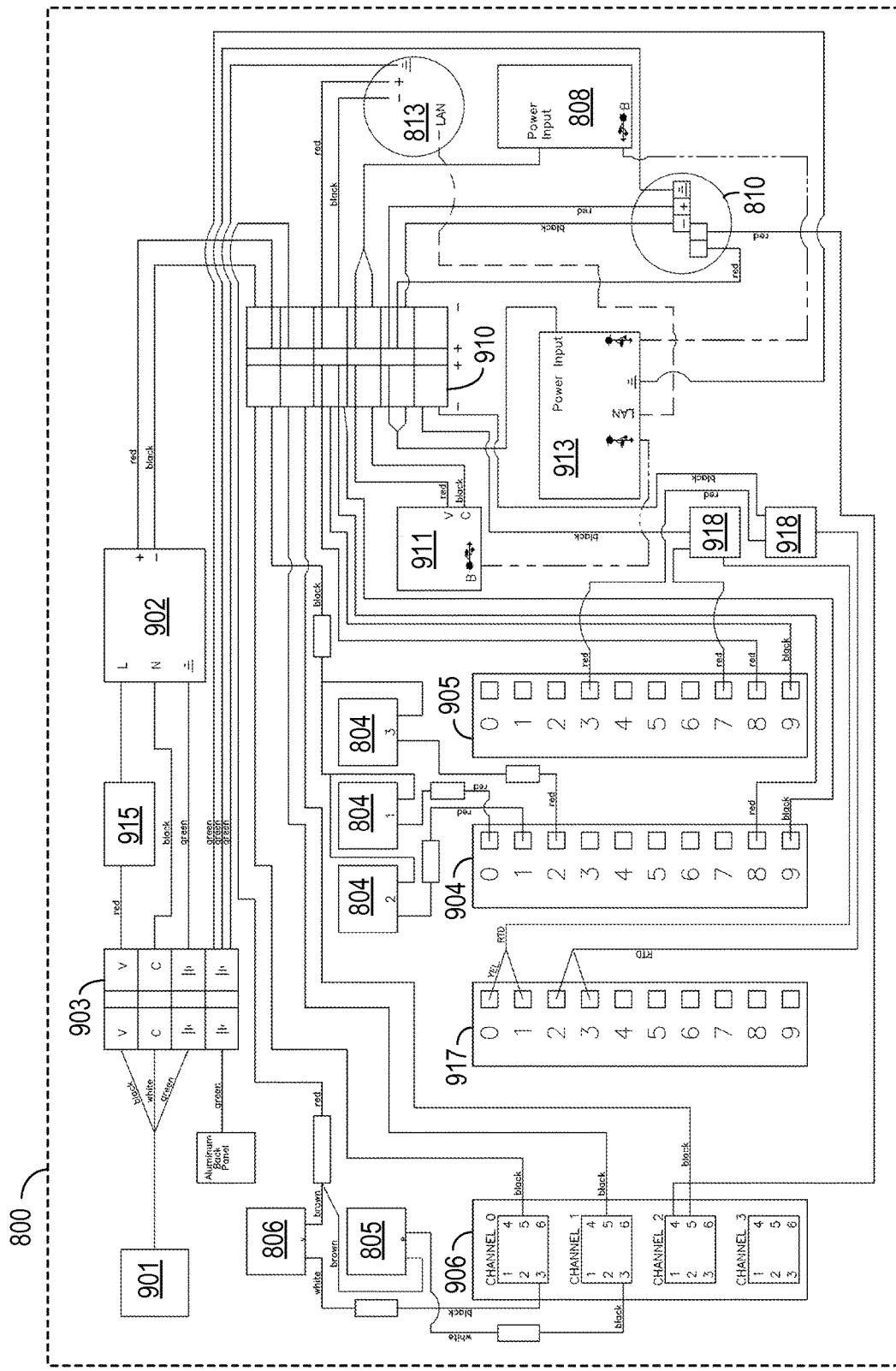
FIG. 9 depicts an example of a wiring diagram for an analyzer with the carrier gas flow path shown in FIG. 8.

FIG. 9 is a schematic diagram showing an example of electrical wiring in analyzer 800, with 120 VAC plug 901, inverter 902, terminal block 903, relays 904 and 905, analog input module 906, 2-way solenoid valves 804, pressure sensor 805, vacuum sensor 806, terminal block 910, data acquisition module 911, syringe/pump assembly 808, computer 913, gas chromatograph 813, emergency stop 915, purge system 810, thermocouple 917, and heater pads 918. A user interface is operatively coupled computer 913. Computer 913 has one or more processors and memory units. The memory unit(s) stores instructions to control gas chromatograph 813, 2-way solenoid valves 804$_1$, 804$_2$, and 804$_3$, and syringe/pump assembly 808. Computer 913 cooperates with gas chromatograph 813, and syringe/pump assembly 808, such that the analyzer operates automatically to collect and analyze samples. Parameters (e.g., the sample stream to be analyzed and the mode of analysis (e.g., static or continuous flow operation) of gas chromatograph 813, the sampling rate and sample volume for the discrete samples to be collected in the composite sample canister, and the number of samples to be collected before the composite sample is provided to the gas chromatograph may be pre-selected or input by a user.

Analyzer 800 may include one or more batteries for self-contained remote operation for a length of time (e.g., from 6-8 hours). In some cases, analyzer 800 has one or more battery back-ups for extended operation. In certain cases, analyzer 800 is powered by line voltage through plug 901.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method comprising:
    collecting, in a vessel coupled to a gas chromatograph and to a conduit through which a fluid is flowing, a first discrete sample of fluid from the conduit, the first discrete sample having a first selected volume;
    collecting, in the vessel and at a first interval from the first discrete sample, a second discrete sample of the fluid from the conduit, the second discrete sample having a second selected volume, thereby forming a composite sample in the vessel while the vessel is coupled to conduit, the composite sample comprising the first discrete sample and the second discrete sample; and
    transferring the composite sample from the vessel to the gas chromatograph.

2. The method of claim 1, further comprising assessing the composition of the composite sample with the gas chromatograph.

3. The method of claim 1, further comprising controlling the collection of the first discrete sample, the collection of the second discrete sample, the transfer of the composite sample, or any combination thereof with a controller.

4. The method of claim 3, further comprising controlling the first selected volume of the first discrete sample and the second selected volume of the second discrete sample with the controller.

5. The method of claim 3, further comprising controlling the first interval with the controller.

6. The method of claim 3, further comprising controlling the controller via a computer operatively coupled to the controller.

7. The method of claim 1, wherein the first selected volume and the second selected volume are user-selectable.

8. The method of claim 1, wherein the gas chromatograph is coupled to the conduit and further comprising transferring a non-composite sample of the fluid flowing through the conduit to the gas chromatograph.

9. The method of claim 8, further comprising assessing the composition of the non-composite sample with the gas chromatograph.

10. The method of claim 1, wherein the first interval is based on elapsed time between the first discrete sample and the second discrete sample or on a volume of fluid flow in the conduit.

11. The method of claim 1, wherein the gas chromatograph is coupled to an additional conduit and receives a sample of additional fluid via the additional conduit.

12. The method of claim 11, further comprising assessing the composition of the sample of the additional fluid with the gas chromatograph.

13. The method of claim 1, further comprising regulating the pressure of the fluid between the conduit and the vessel.

14. The method of claim 1, further comprising collecting, in the vessel and at a second interval from the second discrete sample, a third discrete sample of the fluid from the conduit, the third discrete sample having a third selected volume, thereby forming a composite sample in the vessel while the vessel is coupled to conduit, the composite sample comprising the first discrete sample, the second discrete sample, and the third discrete sample.

15. The method of claim 1, further comprising vaporizing the first discrete sample before collecting the first discrete sample in the vessel.

16. The method of claim 1, further comprising vaporizing the second discrete sample before collecting the second discrete sample in the vessel.

17. The method of claim 1, further comprising vaporizing the composite sample before the fluid is vaporized before transferring the composite sample to the gas chromatograph.

* * * * *